(12) United States Patent
Singh et al.

(10) Patent No.: US 8,299,232 B2
(45) Date of Patent: Oct. 30, 2012

(54) CONSTRUCTING A DNA CHIMERA FOR VACCINE DEVELOPMENT AGAINST LEISHMANIASIS AND TUBERCULOSIS

(75) Inventors: Sarman Singh, New Delhi (IN); Ayan Dey, New Delhi (IN)

(73) Assignees: Department of Biotechnology, New Delhi (IN); All India Institute of Medical Science, New Delhi (IN)

( * ) Notice: Subject to any disclaimer, the term of this patent is extended or adjusted under 35 U.S.C. 154(b) by 0 days.

(21) Appl. No.: 12/995,841

(22) PCT Filed: Feb. 10, 2009

(86) PCT No.: PCT/IN2009/000093
§ 371 (c)(1), (2), (4) Date: Mar. 2, 2011

(87) PCT Pub. No.: WO2010/010577
PCT Pub. Date: Jan. 28, 2010

(65) Prior Publication Data
US 2011/0150932 A1    Jun. 23, 2011

(30) Foreign Application Priority Data
Jul. 25, 2008  (IN) ................ 1751/DEL/08

(51) Int. Cl.
C07H 21/04 (2006.01)
A61K 39/04 (2006.01)
A61K 49/00 (2006.01)

(52) U.S. Cl. ........ 536/23.7; 536/23.1; 424/9.1; 424/9.2; 424/234.1; 424/248.1

(58) Field of Classification Search ................ 536/23.1, 536/23.7; 424/9.1, 9.2, 234.1, 248.1
See application file for complete search history.

(56) References Cited

U.S. PATENT DOCUMENTS

| | | | |
|---|---|---|---|
| 5,674,503 | A | 10/1997 | Olafson |
| 5,736,524 | A | 4/1998 | Content et al. |
| 7,189,399 | B2 | 3/2007 | Bedate et al. |

FOREIGN PATENT DOCUMENTS

| | | |
|---|---|---|
| EP | 1279679 A1 | 1/2003 |
| WO | 2005061730 A1 | 7/2005 |
| WO | 2005063803 A1 | 7/2005 |

*Primary Examiner* — Robert P. Swartz
(74) *Attorney, Agent, or Firm* — The Webb Law Firm

(57) ABSTRACT

A novel recombinant chimera of DNA construct having esat-6 region of *Mycobacterium tuberculosis* and kinesin region of *Leishmania donovani* cloned together on two sides of self cleaving peptide in a DNA vaccine vector pVAX-1 wherein the chimeric construct is operatively linked to a transcriptional promoter thus capable of self replication and expression within the mammalian cell, and the process of preparation thereof comprising: analysis of the predicted protein sequence of kinesin motor domain and esat-6 domain using Promiscuous MHC Class-1 Binding Peptide Prediction Servers; amplification of gene coding for kinesin motor domain and esat-6 domain; cloning of kinesin esat-6 gene region in pGEM-T™ vector for sequence analysis; generation of chimeric construct by directional cloning in pVAX-1 vector. In-vitro expression analysis of kinesin motor domain and esat-6 domain from the clones using cell free translation system and immunogenicity studies; and splenocyte proliferation and cytokines studies using the above mentioned constructs.

5 Claims, 9 Drawing Sheets

Kinesin MHC-1 epitope prediction

MHPSTVRREAERVKVSVRVRPLNERENNAPEGTKVTVAAKQAAAVVTVKVLGGSNNSGAAESM
GTARRVAQDFQFDHVFWSVETPDACGATPATQADVFRTIGYPLVQHAFDGFNSCLFAYGQTGSG
KMYTMMGADVSALSGEGNGVTPRICLEIFARKASVEAQGHSRWIVELGYVEVYNERVSDLLGKR
KKGVKGGGEEVYVDVREHPSRGVFLEGQRLVEVGSLDDVVRLIEIGNGVRHTASTKMNDRSSRS
HAHMLLLREERTMFTKSGETIRTAGKSSRMNLVDLAGSKRVAQSQVEGQQFKEATHINLSLTTLG
RVIDVLADMATKGAKAQYSVAPFRDSKLTFILKDSLGGNSKTFMIATVSPSALNYEETLSTLRYAS
RARDIVNVAQVNEDPRARRIRELEEQMEDMRQAMAGGDPAYVSELKKKLALLESEAQKRAADL
QALERERHNQVQERLLRATEAEKSELESRAAALQEEMTATRRQADKMQALNLRLKEEQARKER
ELLKEMAKKDAALSKVRQRKDAEIASEREKLESTVAQLEREQREREVALDALQTHQRKLQEALES
SERTAAERDQLLQQLTELQSERTQLSQVVTDRERLTRDLQRIQYEYGETELARDVALCAAQEMEA
RYHAAVFHLQTLLELATEWEDALRERALAERDEAAAAELDAAASTSQNARESACERLTSLEQQL
RDSEERAAELMRKLEATAAAKSSAEQDRENTRATLEQQLRESEEHAAELKAQLESTAAAKTSAEQ
DRENTRAALEQRLRESEERAAELASQLEATAAAKSSAEQDRENTRATLEQQLRESEARAAELASQ
LESTAAAKSSAEQDRENTRAT

```
------------------------------------AAESMGTAR------------SVETPDACG------------
------------------GADVSALSG---------------SVEAQGHSR-IVELGYVEV----VSDLLGKRK----------
---------------LIEIGNGVR---------------------------------LVDLAGSKR--------------
----------SVAPFRDSK---------------TVSPSALNY-----------------VNEDPRARR-----------
-----VSELKKKLA---ESEAQKRAA-------------------ATEAEKSEL---------LQEEMTATR-----------
------------------KLESTVAQL---------------------SSERTAAER------LTELQSERT-------
VTDRERLTR----------ETELARDVA---AAQEMEARY----------------ATEWEDALR------------AAELDAAAS-
------------------DSEERAAEL---KLEATAAAK---------------------ESEEHAAEL---QLESTAAAK-------------
----ESEERAAEL---QLEATAAAK-----------------ESEARAAEL---QLESTAAAK---------
-----------------------------------------------------------------------
-----------------------------------------------------------------------
------------------------LLESEAQKR-------------KSELESRAA--------------
-----------------------------------------------------------------------
TRDLQRIQY---------------------------------------------------------------
-----------------------------------------------------------------------
-----------------------------------------------------------------------
-----------------------------------------------------------------------
-------------------AADLQALER-----------ELESRAAAL----------
-----------------------------------------------------------------------
```

ESAT-6 MHC-1 epitope prediction

MTEQQWNFAGIEAAASAIQGNVTSIHSLLDEGKQSLTKLAAAWGGSGSEAYQGVQQKWDATATE
LNNALQNLARTISEAGQAMASTEGNVTGMFA

```
-----WNFAGIEAA-----GNVTSIHSL------QSLTKLAAA----------QGVQQKWDA--
TELNNALQN---RTISEAGQA---TEGNVTGMF---------AGIEAAASA------------------
-------------------ATATELNNA---------SEAGQAMAS--------- (SEQ ID NO: 5)
```

Figure 1 - Analysis of the predicted protein sequence of Kinesin motor domain and ESAT-6 domain using Promiscuous MHC Class-1 Binding Peptide Prediction Servers.

(A)

M-1 Kb Marker

Lane 1- negative control

Lane 2- Amplified Kinesin motor Domain

Lane 3- Amplified Kinesin motor Domain (B)

M- 100 bp Marker

Lane 1- Amplified *esat-6* domain

Lane 2- Amplified *esat-6* domain

Lane 3 & 4- Amplified *esat-6* domain

Lane 5- Negative control

Figure 2: A) Amplification of kinesin motor domain, B) Amplification of *esat-6* region.

M- 100 bp Marker
1&4- Clones having kinesin Motor Domain
5- Clone having *esat-6* (Rv-3875) gene
2, 3 & 6- Empty Plasmid Figure 3: Restriction analysis of the clones having the motor domain region of kinesin gene of *Leishmania donovani* and *esat-6* region of *Mycobacterium tuberculosis* cloned separately in pGEM-T vector for sequencing and verification.

5' ——————————————————— 3'

ESAT-6     2A peptide     kinesin

Gene Expression

ESAT-6 Peptide     FMDV peptide (degraded)     Kinesin Peptide

Figure 4: Chimera Generation esat-6 region of M. tuberculosis
FMDV 2A peptide
Kinesin gene of L. donovani (KE-16)
CMV Promoter Region
Multiple Cloning Site
Poly A' Termination region
pVAX1-LDMT Restriction Sites
A- Hind-III
B- BamH-I
C- BstX-I
D- Apa-I Figure-5: Cloning strategy for generation of pVAX1-LDMT 1   2   3   4   5   6   7   8

- Chimera with Kinesin (BstX1 & Apa 1)
- Chimera with Kinesin (BstX1 & Apa1)
- Chimera with Kinesin (BamH1 & Apa1)
- Chimera with ESAT-6 (Hind III & BamH1)
- Chimera with Kinesin (BstX1 & Apa1)
- Chimera with esat-6 (Hind III & BamH1)
- Chimera with esat-6 (Hind III & BamH1)
- 100 bp Marker (MBI®)

Figure 6: Restriction analysis of the chimeric pVAX-1® clones having kinesin motor domain region and esat-6 region cloned together on two side of self cleaving FMDV-2A peptide.

(7A)  (7B)

Figure 7A & 7B: Restriction analysis of the individual pVAX-1® clones having kinesin motor domain region and *esat-6* region cloned separately.

| | M | 1 | 2 | 3 | 4 |

117 Kda
90 Kda
49 Kda
36 Kda → Kinesin
26 Kda
19 Kda

M- Prestained Molecular Weight Marker (MBI ®)
1- *In-vitro* expression of Kinesin from Chimeric construct
2- *In-vitro* expression of Kinesin from Chimera construct
3- *In-vitro* expression of Kinesin from individual Kinesin-pVAX1construct
4- Purified rLvacc probed with VL positive patient serum

Figure 8A: *In- vitro* expression of Kinesin motor domain.

M- Prestained Molecular Weight Marker (NEB®)
1- *In-vitro* expression of ESAT-6 from Chimeric construct
2- *In-vitro* expression of ESAT-6 from Chimera construct
3- *In-vitro* expression of ESAT-6 from individual ESAT-6-pVAX1 construct
4- Purified ESAT-6 probed with TB positive patient serum

Figure 8B: *In- vitro* expression of ESAT-6 domain.

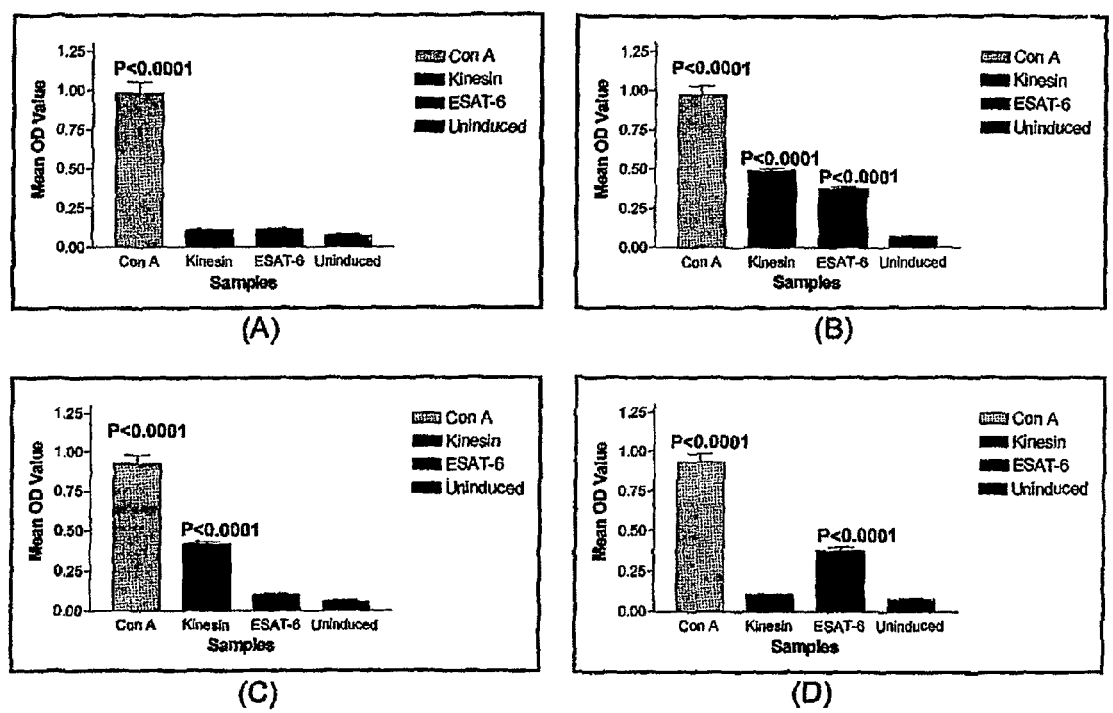
Figure 9: Splenocytes Proliferation in response to Kinesin Motor Domain and ESAT-6 in (A) Empty Plasmid; (B) Chimeric construct; (C) Kinesin Motor Domain construct; (D) esat-6 construct vaccinated mice group.

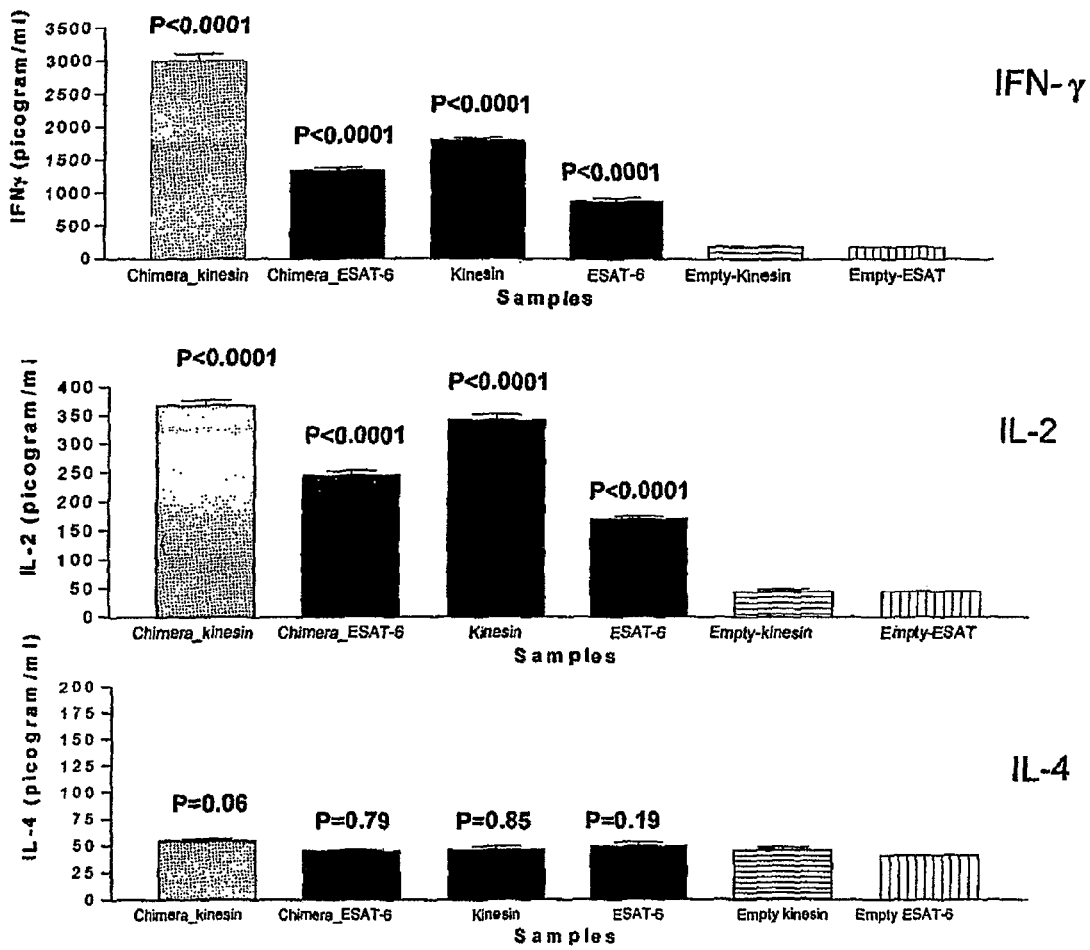
Figure 10: IFN-γ, IL-2 and IL-4 production by Splenocytes from mice vaccinated either with chimera or individual vaccine candidates and their response to the specific antigen (Kinesin and ESAT-6) stimulation.

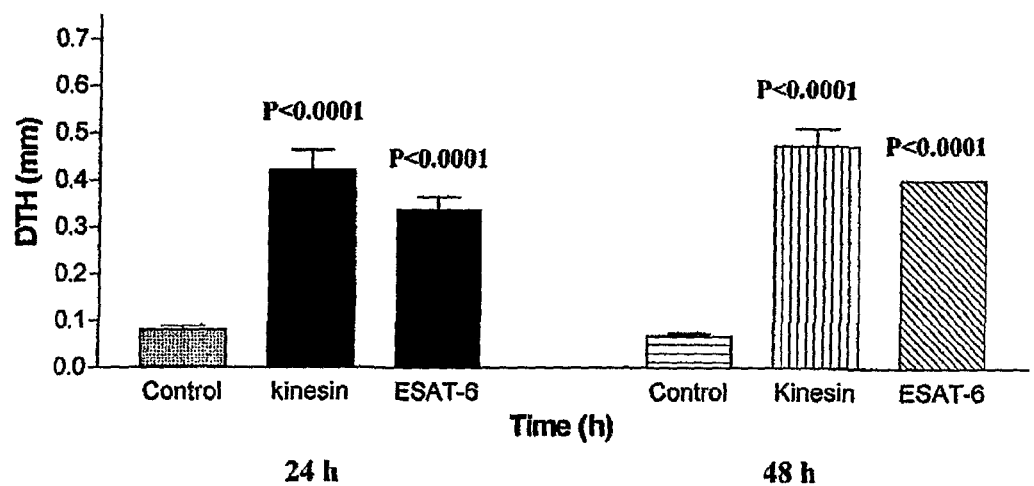
Figure 11: DTH response to kinesin motor domain and ESAT-6 in chimeric vaccine construct injected mice group

SEQUENCE LISTING

<160> NUMBER OF SEQ ID NOS: 9

<210> SEQ ID NO 1
<211> LENGTH: 975
<212> TYPE: DNA
<213> ORGANISM: Leishmania donovani

<400> SEQUENCE: 1
atgcaccctt ccactgtgcg gcgtgaggcg gagcgggtga aggtgtcggt gcgcgtgcgc 60
cccctaaacg aacgtgaaaa caatgccccg gaagggacga aagtgaccgt tgcggcgaaa 120
caggcggccg ccgtggtgac ggtcaaggtc ctgggaggca gcaacaacag cggcgccgcc 180
gagtcgatgg ggactgcaag gcgggtagcg caggactttc agttcgacca cgtgttctgg 240
tctgtggaga cgccggacgc gtgcggcgcg acccccgcga cgcaggcaga cgtgttccgg 300
acgatcgggt acccgctggt gcagcacgcg ttcgacgggt tcaactcgtg cttgtttgcg 360
tacgggcaga cagggagcgg gaagatgtac acgatgatgg gcgcggacgt gagcgcgctt 420
agtggtgagg gcaacggcgt gacgccgcgg atctgcctgg agatctttgc gcggaaggcg 480
agcgtggagg cgcaggggca ctcgcggtgg atcgtggagc tggggtacgt ggaggtgtac 540
aacgagcgcg tgtcggacct gcttgggaag cggaagaagg gtgtgaaggg cggcggcgag 600
gaggtgtacg tggacgtgcg cgagcacccg agccgcggcg tgttcctgga ggggcagcgg 660
ctggtggagg ttgggagcct ggacgatgtt gtgcggctga tcgagatcgg caacggcgtg 720

-continued

```
cggcacaccg cttcaacgaa gatgaacgac cggagcagcc ggagccacgc gatcatcatg    780
ctgctgctgc gcgaggagcg gacgatgacg acgaagagcg gggagacgat ccgtactgcc    840
ggcaagagca gccgcatgaa ccttgtggac cttgcggggt ctaagcgcgt ggcgcagtcg    900
caggtggagg ggcagcagtt caaggaggcg acgcacatca acctgtcgct gacgacgctc    960
gggcgcgtga tcgac                                                    975
```

<210> SEQ ID NO 2
<211> LENGTH: 282
<212> TYPE: DNA
<213> ORGANISM: Mycobacterium tuberculosis

<400> SEQUENCE: 2

```
atgacagagc agcagtggaa tttcgcgggt atcgaggccg cggcaagcgc aatccaggga     60
aatgtcacgt ccatattccc tccttgacga ggggaagcag tccctgacca agctcgcagc    120
ggcctggggc ggtagcggtt cggaggcgtc cagggtgtcc agcaaaaatg gacgccacg    180 gctaccgagc tgaacaacgc gctgcagaac ctggcgcgga cgatcagcga agccggtcag    240
gcaatggctt cgaccgaagg caacgtcact gggatgttcg ca                      282
```

<210> SEQ ID NO 3
<211> LENGTH: 80
<212> TYPE: DNA
<213> ORGANISM: Foot-and-mouth disease virus

<400> SEQUENCE: 3

```
gcggatccag agccgagggc aggggaagtc ttctaacatg cggggacgtg gaggaaaatc     60
ccccaatgca ttggatgcat                                                80
```

<210> SEQ ID NO 4
<211> LENGTH: 1372
<212> TYPE: DNA
<213> ORGANISM: Artificial Sequence
<220> FEATURE:
<223> OTHER INFORMATION: Chimeric Construct of Kinesin motor domain
      gene, esat-6 gene and FMDV 2A peptide gene

<400> SEQUENCE: 4

```
cccaagctta tgacagagca gcagtggaat ttcgcgggta tcgaggccgc ggcaagcgca     60
atccagggaa atgtcacgtc catattccct ccttgacgag gggaagcagt ccctgaccaa    120
gctcgcagcg gcctggggcg gtagcggttc ggaggcgtcc agggtgtcca gcaaaaatgg    180
gacgccacgg ctaccgagct gaacaacgcg ctgcagaacc tggcgcggac gatcagcgaa    240
gccggtcagg caatggcttc gaccgaaggc aacgtcactg ggatgttcgc aggatccgcg    300
cggatccaga gccgagggca ggggaagtct tctaacatgc ggggacgtgg aggaaaatcc    360
cccaatgcat tggatgcatc caatgcattg gatgcaccct ccactgtgc ggcgtgaggc    420 ggagcgggtg aaggtgtcgg tgcgcgtgcg ccccctaaac gaacgtgaaa caatgcccc    480 ggaagggacg aaagtgaccg ttgcggcgaa acaggcggcc gccgtggtga cggtcaaggt    540
cctgggaggc agcaacaaca gcggcgccgc cgagtcgatg gggactgcaa ggcgggtagc    600
gcaggacttt cagttcgacc acgtgttctg gtctgtggag acgccggacg cgtgcggcgc    660 gaccccgcg acgcaggcag acgtgttccg gacgatcggg tacccgctgg tgcagcacgc    720
gttcgacggg ttcaactcgt gcttgtttgc gtacgggcag acaggagcg ggaagatgta    780 cacgatgatg ggcgcggacg tgagcgcgct tagtggtgag gcaacgcgcg tgacgccgcg    840
gatctgcctg gagatctttg cgcggaaggc gagcgtggag gcgcaggggc actcgcggtg    900
```

-continued

```
gatcgtggag ctggggtacg tggaggtgta caacgagcgc gtgtcggacc tgcttgggaa    960
gcggaagaag ggtgtgaagg gcggcggcga ggaggtgtac gtggacgtgc gcgagcaccc   1020
gagccgcggc gtgttcctgg aggggcagcg gctggtggag gttgggagcc tggacgatgt   1080
tgtgcggctg atcgagatcg gcaacggcgt gcggcacacc gcttcaacga agatgaacga   1140
ccggagcagc cggagccacg cgatcatcat gctgctgctg cgcgaggagc ggacgatgac   1200
gacgaagagc ggggagacga tccgtactgc cggcaagagc agccgcatga accttgtgga   1260
ccttgcgggg tctaagcgcg tggcgcagtc gcaggtggag gggcagcagt tcaaggaggc   1320
gacgcacatc aacctgtcgc tgacgacgct cgggcgcgtg atcgacgggc cc           1372
```

<210> SEQ ID NO 5
<211> LENGTH: 441
<212> TYPE: PRT
<213> ORGANISM: Artificial Sequence
<220> FEATURE:
<223> OTHER INFORMATION: Chimeric Construct of Kinesin motor domain
      gene, esat-6 gene and FMDV 2A peptide gene

<400> SEQUENCE: 5

```
Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala Arg
                85                  90                  95

Ala Glu Gly Arg Gly Ser Leu Leu Thr Cys Gly Asp Val Glu Glu Asn
            100                 105                 110

Pro Gly Pro Met His Pro Ser Thr Val Arg Arg Glu Ala Glu Arg Val
        115                 120                 125

Lys Val Ser Val Arg Val Arg Pro Leu Asn Glu Arg Glu Asn Asn Ala
    130                 135                 140

Pro Glu Gly Thr Lys Val Thr Val Ala Ala Lys Gln Ala Ala Ala Val
145                 150                 155                 160

Val Thr Val Lys Val Leu Gly Gly Ser Asn Asn Ser Gly Ala Ala Glu
                165                 170                 175

Ser Met Gly Thr Ala Arg Arg Val Ala Gln Asp Phe Gln Phe Asp His
            180                 185                 190

Val Phe Trp Ser Val Glu Thr Pro Asp Ala Cys Gly Ala Thr Pro Ala
        195                 200                 205

Thr Gln Ala Asp Val Phe Arg Thr Ile Gly Tyr Pro Leu Val Gln His
    210                 215                 220

Ala Phe Asp Gly Phe Asn Ser Cys Leu Phe Ala Tyr Gly Gln Thr Gly
225                 230                 235                 240

Ser Gly Lys Met Tyr Thr Met Met Gly Ala Asp Val Ser Ala Leu Ser
                245                 250                 255

Gly Glu Gly Asn Gly Val Thr Pro Arg Ile Cys Leu Glu Ile Phe Ala
            260                 265                 270

Arg Lys Ala Ser Val Glu Ala Gln Gly His Ser Arg Trp Leu Val Glu
```

```
                275                 280                 285

Leu Gly Tyr Val Glu Val Tyr Asn Glu Arg Val Ser Asp Leu Leu Gly
    290                 295                 300

Lys Arg Lys Lys Gly Val Lys Gly Gly Glu Glu Val Tyr Val Asp
305                 310                 315                 320

Val Arg Glu His Pro Ser Arg Gly Val Phe Leu Glu Gly Gln Arg Leu
                325                 330                 335

Val Glu Val Gly Ser Leu Asp Asp Val Val Arg Leu Ile Glu Ile Gly
            340                 345                 350

Asn Gly Val Arg Leu Ile Thr Ala Ser Thr Lys Met Asn Asp Arg Ser
        355                 360                 365

Ser Arg Ser His Ala Ile Ile Met Leu Leu Leu Arg Glu Glu Arg Thr
    370                 375                 380

Met Thr Thr Lys Ser Gly Glu Thr Ile Arg Thr Ala Gly Lys Ser Ser
385                 390                 395                 400

Arg Met Asn Leu Val Asp Leu Ala Gly Ser Lys Arg Val Ala Gln Ser
                405                 410                 415

Gln Val Glu Gly Gln Gln Phe Lys Glu Ala Thr His Ile Asn Leu Ser
            420                 425                 430

Leu Thr Thr Leu Gly Arg Val Ile Asp
        435                 440

<210> SEQ ID NO 6
<211> LENGTH: 33
<212> TYPE: DNA
<213> ORGANISM: Artificial Sequence
<220> FEATURE:
<223> OTHER INFORMATION: Oligonucleotide for L. donovani kinesin motor
      domain gene

<400> SEQUENCE: 6
ccaatgcatt ggatgcaccc ttccactgtg cgg                                33

<210> SEQ ID NO 7
<211> LENGTH: 30
<212> TYPE: DNA
<213> ORGANISM: Artificial Sequence
<220> FEATURE:
<223> OTHER INFORMATION: Synthetic Oligonucleotide of L. donovani
      kinesin motor domain gene

<400> SEQUENCE: 7
gggcccgtcg atcacgcgcc cgagcgtcgt                                    30

<210> SEQ ID NO 8
<211> LENGTH: 28
<212> TYPE: DNA
<213> ORGANISM: Artificial Sequence
<220> FEATURE:
<223> OTHER INFORMATION: Synthetic Oligonucleotide for M. tuberculosis
      esat-6 gene

<400> SEQUENCE: 8
cccaagctta tgacagagca gcagtgga                                      28

<210> SEQ ID NO 9
<211> LENGTH: 27
<212> TYPE: DNA
<213> ORGANISM: Artificial Sequence
<220> FEATURE:
<223> OTHER INFORMATION: Synthetic Oligonucleotide for amplification of
      M. tuberculosis esat-6 gene
```

```
<400> SEQUENCE: 9
gcggatcctg cgaacatccc agtgacg                                              27
```

CONSTRUCTING A DNA CHIMERA FOR VACCINE DEVELOPMENT AGAINST LEISHMANIASIS AND TUBERCULOSIS

CROSS-REFERENCE TO RELATED APPLICATIONS

This application claims priority to International Application No. PCT/IN2009/000093 filed on Feb. 10, 2009, which is a PCT application claiming priority to Indian Application No. 1751/DEL/08 filed on Jul. 25, 2008, all of which are incorporated herein by reference in their entireties.

FIELD OF INVENTION

The invention provides novel chimeric DNA vaccine construct having esat-6 region of *Mycobacterium tuberculosis* and kinesin motor domain region of *Leishmania donovani* cloned together on two sides of self cleaving peptide in a DNA vaccine vector capable of replicating inside mammalian host cells. The construct is intended to be used for protection against leishmaniasis and tuberculosis.

BACKGROUND OF INVENTION

Over the past 100 years, the development and widespread use of vaccines against infectious agents has been one of the triumphs of medical science. One reason for the success of these vaccines is that they excel at inducing antibody production (humoral immunity), which are the principle components of immune protection against most viruses and bacteria. There are, however exceptions, including medically important intracellular organisms like *Mycobacterium tuberculosis*, the malaria parasite, Leishmania parasite, and possibly the human immunodeficiency virus (HIV), in which protection depends more on cell-mediated immunity than on the induction of antibodies (humoral immunity).

The conventional active vaccines are made either of a killed or attenuated form of the infectious agent. Also a modified product of the infectious agent (toxoid) or a constituent of an infectious agent (such as the capsule) is used. These vaccines have some limitations and problem with the antibody response they induce. Moreover, large and repeated doses are required to administer when a non-viable (killed, attenuated organism, toxoid or capsule) vaccine is used and the protective immunity obtained is not long lasting. Furthermore, the process of manufacturing live attenuated vaccine and killed vaccines can alter the structure of native protein and thus lower the antigenecity of the vaccine and in most cases usually a humoral but not a cell-mediated immune response is generated. What is required in such cases, but not available, are antigens that are safe to use, that can be processed by the endogenous pathway and eventually activate cytotoxic T-lymphocytes (CTL). This becomes highly desirable for intracellular pathogens such as *Leishmania* parasite. The activated CTL generated in this way would destroy the parasite-infected cell.

For these reasons, new approaches of vaccination are under intensive investigations that involve the injection of a piece of DNA that contains the gene for the antigen of interest. Various recent reports of induction of cellular immune responses by a DNA vaccine against various parasites including Plasmodium and Leishmania, and to various bacterial species such as *Mycobacterium spp* in humans raises hope for the clinical applicability of this method of immunization.

In a DNA vaccine, the gene for the desired antigen (pathogen origin) of interest is cloned into a bacterial plasmid that is engineered to augment the expression of the inserted gene in mammalian cells. After being injected into an animal, the plasmid enters host cells, where it remains in the nucleus as an episome; without getting integrated into the host cell DNA. Using the host cell's metabolic machinery, the inserted clone DNA in the episome directs the synthesis of the antigen it encodes.

An approach involving the synthesis of antigen within the cells has several potential advantages over immunization with exogeneous recombinant proteins or killed organisms. A protein produced by plasmid-transfected cells is likely to be folded in its native configuration, which favors the production of neutralizing antibodies. Furthermore, the peptide synthesized under the direction of the plasmid DNA can be brought to the surface of cells and displayed by MHC class I molecules, an essential step in the stimulation of $CD8^+$ cytotoxic T cells, which further evokes cell mediated immunity. On contrast, standard vaccine antigens are taken up into cells by phagocytosis or endocytosis and are processed through the MHC class II system, which primarily stimulates antibody response. Finally, DNA vaccines have be shown to persist and stimulate sustained immune responses.

In addition to being able to induce the appropriate immune responses, DNA vaccines are also attractive because they ensure appropriate folding of the polypeptide, produce and release the antigen over long periods, and do not require adjuvants. Other advantages include the stability of the DNA molecule, long shelf life, and do not require a strict cold chain for distribution. DNA vaccines are also safer than certain live-virus vaccines, for use in immuno compromised patients such as those infected with HIV. It also bypasses the numerous problems associated with conventional vaccines, such as immune responses against the delivery vector and concerns about safety related to the use of viral vectors. They DNA vaccines can be constructed in such a way that the genes from different pathogens are included in the same plasmid, thus potentially decreasing the number of vaccinations required for children. Moreover in tropical countries like ours where people usually suffer from more than one type of infection, chimeric vaccines have become an important need.

Both *Leishmania* and *Mycobacterium* are considered to be important human pathogen. The world health organization (WHO) considers leishmaniasis to b one of the important parasitic diseases with approximately 350 million people at risk of contracting the disease. The disease has worldwide distribution, and is endemic in at least 88 countries, and the disease occurs on all continents except Antarctica were no suitable vectors are present. On the other hand Mycobacterial infections remain major cause of mortality and morbidity worldwide. Tuberculosis causes 2-3 millions deaths and 15 million new cases per annum worldwide, while more than 1000 people die off every day in India.

Considering the treatment, drug resistant tuberculosis and drug resistant leishmaniasis have become a major health problem. Particularly of interest is multidrug resistance tuberculosis, where the patients become insensitive to different drugs. Today treatment of leishmaniasis also constitutes a difficult challenge due to co-infection with HIV and resistance to pentavalent antimonials (most common, affordable drug against leishmaniasis). The problem becomes more severe due to poverty and malnutrition, migration of non-immune refugees, insufficient diagnostic tools and unavoidable or unaffordable drugs.

While the relationship between HIV/TB and HIV/Leishmaniasis has been documented, little is known about TB/*Leishmania* co-infection, a syndrome that has important clinical implications. Although distinct in aetiology and transmission mechanisms, VL and TB share several features. The most important is that both are intracellular in nature and cell mediated immunity plays important role in protection against infection. Moreover, in both cases infectious remain asymptomatic in several infected persons. Symptoms usually develop after several months or years and progress to clinical disease. Very long incubation periods (latent infection) may be related to immune suppression occurring at a later age, which apparently turns the latent infection into active disease.

It is reported that Tuberculosis (TB) can cause immunosuppression by blocking macrophage response to IFN-γ by inhibiting the transcription of IFN-γ-responsive genes, which results in the progression of latent leishmanial infection to clinical manifestation. *Mycobacterium* also involves in the down-regulation of the Ag-presenting molecule CD1 from the cell surface of CD1+ APCs. The loss of CD1 from the cell surface is associated with a complete inhibition of the ability of the infected cells to present Ag to CD1-restricted dendritic cells, which can initiate antimicrobial responses by CD1-mediated presentation of pathogen-derived glycolipids.

Similarly, VL can reactivate a latent mycobacterial infection, *Leishmania* is known to downmodulate Nitric Oxide production, correlated with a reduction in inducible nitric oxide synthase (iNOS) activity. *Leishmania* like Mycobacteria inhibits CD1 expression and prevents activation of CD1-restricted T cells by dendritic cells. Evasion of presentation by CD1 may represent a *Leishmania* survival strategy to avoid recognition of abundant parasite glycolipids. Moreover, it have also been observed that *Leishmania* infected macrophages are less efficient at promoting the sustained TCR signaling necessary for activation of T cell and for IFN-γ production.

In the present situation it has become imperative to control co-infection cases particularly in areas where both leishmaniasis and tuberculosis occur concomitantly. The development of chimeric vaccine will provide an effective strategy in controlling leishmaniasis and Mycobacterial infection and further reducing the number of vaccination required. Moreover, vaccinations have an added advantage of avoiding the problem encountered with drug resistance.

As far as development of various specific vaccines is concerned for leishmaniasis numerous antigens have been tested with variable success rates using in vitro and mouse models. Among the various vaccines developed to date, heat killed vaccines are the most popular one. The first study was of a double blind randomized trial in which a pool of five strains of merthiolate-killed *L. major* was used as vaccine. The results showed that the protection against cutaneous Leishmaniasis was 23% and 60% in placebo and vaccine arms, respectively. Similar strategy was used in India also at CDRI Lucknow, using heat killed (autoclaved) *L. donovani* along with *Mycobacterium habana* and *L. major* along with BCG were used as a vaccine against visceral and cutaneous leishmaniasis. The vaccine shows good protective efficacy but the major problem with the vaccine is that the antigen alone produces only marginal protection and requires BCG as adjuvant; moreover it causes localized allergic reaction at site of inoculation. Although the single dose of vaccine was protective in monkeys. However, all animals did have occasional parasites, even on day 90 post inoculation.

In Iran, a mixed BCG *L. major* killed vaccine has also undergone clinical trials for safety and efficacy. Although it proved safe, its efficacy was only 35%.

The relative merits of live-attenuated vaccines versus killed vaccines have been a constant subject of debate in relation to many antimicrobial and viral vaccines. The most notable arguments have been those concerned with immunogenicity, efficacy, safety, ease of production and distribution, and stability. The absence of a clear genetic profile of any Leishmania strain that can be labeled as a virulent, has kept the possibility of using live attenuated vaccine at abeyance. But recent advances to manipulate the Leishmania genome by introducing or eliminating genes have opened the avenues and potential to generate live-attenuated vaccines. It is now possible to generate parasites lacking genes essential for long-term survival in the mammalian host, e.g. by deleting the gene encoding the enzyme dihydrofolate reductase-thymidylate synthetase (DHFR-TS). In a mouse model, *L. major* parasites lacking DHFR-TS induce protection against the infection of *L. major* and *L. amazonensis*. However the disadvantages of such vaccine are its large-scale production and distribution in the field. Also no study has been done to evaluate its protection efficacy against *L. donovani*.

The newer vaccines under consideration comprise of recombinant DNA-derived antigens and peptides. Some of the target antigens are species ad life cycle stage specific, while others are shared by promastigotes and amastigotes. Some are conserved among *Leshmania* species, while others are not. Also another biggest advantage is that these vaccines can be delivered as purified immunogens, because the naked DNA encodes them. Genetic manipulations can also allow us to target these antigens to specific locations or to particular antigen-presenting cells, such as dendritic cells or Langerhans cells, which are considered to be essential for the initiation of primary T-cell responses.

The first recombinant antigen used as vaccine against leishmaniasis was leishmaniolysin or gp63. This is a membrane ecto-metalloprotease present in promastigotes of all species. The gp63 is also one of the parasite receptors for host macrophages, and parasite mutants lacking the protein are reported to be avirulent. Gp63 is known to help promastigotes by rendering them resistant to complement-mediated cytolysis. It also appears to act, (perhaps, together with LPG), namely infection of macrophages by promastigotes via receptor-mediated endocytosis. However, the efficacy was found to be only 50% and that too at higher concentration. Several factors may account for this. The antigen needs to be in their native conformation for processing, and *Escherichia coli*-derived recombinant proteins may not fulfill this requirement. Another reason for the low success rate could be that some polypeptides might be minor immunogen only. Apart from gp63, other antigens like LACK and A2 were also tested, but the results are not satisfactory. Failure of this single antigen vaccines leads to development of conjugate polypeptide vaccines. One such candidate is recombinant polyprotein comprising a tandem fusion of the leishmanial antigens thiol-specific antioxidant, *L. major* stress-inducible protein 1 (LmSTI1), and Leishmania elongation initiation factor (LeIF) delivered with monophosphoryl lipid A-squalene (MPL-SE) suitable for human use. This vaccine candidate is the first defined vaccine for cutaneous leishmaniasis in human clinical trials and has completed phase 1 and 2 safety and immunogenecity testing in normal, healthy human subjects. The vaccine candidate also show good protective efficacy against visceral leishmaniasis in hamster model.

Naked DNA vaccines have become popular recently and revolutionized the prevention and treatment strategies against infectious diseases, particularly against viruses and bacteria. However, DNA vaccines have not made much in-road in the field of medical parasitology except against malaria, to some extent. In India work on DNA vaccine against *Leishmania donovani* is in progress. Vaccination with ORFF gene induced both humoral and cellular immune response against ORFF, which provided a significant level of protection against challenge with *L. donovani* in mouse model. However no further studies involving efficacy studies in primates model or phase trials have been done for its application in human.

For developing vaccine against Mycobacterium, immunization work is done mainly on the vaccine strain of *M. bovis* [Bacilli Calmette-Guerin (BCG)] that provides partial but variable, protection against tuberculosis and leprosy. BCG is derived from attenuation of an isolated strain of *Mycobacterium bovis*. It was introduced as a tuberculosis vaccine for humans in 1921 and has been relatively safe with rare incidences of adverse reactions. BCG vaccination has been shown in some studies to effectively boost the immune response against primary infection but has limited effect on subsequent course of dormancy and reactivation. Little or no protection is seen after 10 to 15 years which suggests that childhood vaccination will not prevent adult re-infection.

Safety of the BCG vaccine is a growing concern after epidemic of HIV. In order to avoid potential adverse effects of BCG within immunocompromised individuals, BCG auxotrophs have been developed using the previously mentioned technique. Auxotrophs are mutants that require a specific nutrient or metabolite that is not required by the wild type. As a result, such mutants can only survive for a short period of time within a host, if the host lacks the specified nutrient. Five such strains were tested in mice with severe combined immunodeficiency disease (SCID) for safety, and in a susceptible strain of mice for protection. Results have shown that these strains are safe in SCID mice, and demonstrate the same amount of protective immunity as normal BCG in susceptible mice, suggesting that this could be a safer method of vaccination.

An innovative vaccine approach currently being applied in the search for a BCG replacement is the protein or DNA vaccine. This includes a number of protein and DNA molecules expressing single Mycobacterial antigen that could induce partial protection against experimental infection with *M. tuberculosisl*. Some of these antigens are those proteins that are secreted by *Mycobacterium* during their residence in macrophages, such as: i) the antigen 85 complex of proteins (85A, 85B, 85C), ii) a 6 kDa protein termed Early Secreted Antigenic Target (ESAT-6), iii) a 38 kDa lipoprotein with homology to PhoS, iv) the 65 kDa heat-shock protein (Hsp 65) v) a 55 kDa protein rich in proline and threonine and vi) a 19 kDa lipoprotein.

The applicant also did an extensive search and found that although various vaccine candidates have been developed against visceral leishmaniasis and tuberculosis but none of them was developed as chimera of *L. donovani* and *M tuberculosis* with SEQ ID No. 1 and SEQ ID No. 2.

Discussed below are the few US patents on chimeric constructs, DNA and recombinant polypeptide vaccine constructs on the subject concerned and the uniqueness of the applicants' construct.

The disclosed a chimera of polypeptide from *Leishmania infantuml*. However the present invention is chimera of polynucleotide.

The WIPO Patent no. WO/2006/053485 by Zhongming, in Nov. 14, 2005 teaches about a chimeric *mycobacterium tuberculosis* gene vaccine and the preparation method thereof. A chimeric *mycobacterium tuberculosis* gene vaccine is provided. The vaccine comprises Ag85a gene encoding a structural protein of *Mycobacterium tuberculosis* and ESAT6 gene of *Mycobacterium tuberculosis*, wherein the ESAT6 gene is inserted into the sequence of Ag85a gene, and the Ag85a gene is inserted to eukaryotic expression vector pVAX1. The composition of the invention is useful for inducing the immune system in mice and monkey.

The above disclosed a chimera vaccine for control of tuberculosis only. Moreover, the antigen the chimeric construct express was a conjugated chimeric peptide. However, the present invention provides chimera of Kinesin motor domain and esat-6 gene useful in control of leishmaniasis and tuberculosis both. Also the construct is designed in such a way that it allows individual expression of both the gene from chimeric construct, instead of generation of chimeric peptide.

The European Patent No. EP1279679 by Soto at al., in Jan. 29, 2003 teaches about A composition and method for stimulating an immune response against an antigen in immunized individuals or in cell groups. The composition comprises a protein called Lip2a *Leishmania* formed by a sequence of amino acids coded for by a sequence of DNA. The compositions of the invention are useful for promoting a humoral or cellular response in the individual who is inoculated with said compositions. The invention does not deal with either chimera molecular or with SEQ ID No. 1 and SEQ ID No. 2

The U.S. Pat. No. 5,674,503 by Olafson in Oct. 7, 1997 teaches about Peptides capable of eliciting an immune response to leishmaniasis and methods of using the same. The invention provides a pharmaceutical composition comprising the peptides or immunogens, in combination with a physiologically acceptable carrier or diluent. However applicant's present invention does no deal with peptides.

The U.S. Pat. No. 5,736,524 by Content et al., in Apr. 7, 1998 teaches about Polynucleotide tuberculosis vaccine. This invention provides DNA construct which, when directly introduced into a vertebrate in vivo, including mammals such as humans induces the expression of encoded proteins within the animal. The result, as shown in this disclosure, is induction of immune responses against M.tb. Polynucleotides for the purpose of generating protective immune responses against M.tb infection.

The above although disclosed a DNA vaccine but it does deal with chimera. Moreover it is useful for control of tuberculosis only.

OBJECT OF THE INVENTION

The main object of this invention is to develop a chimeric DNA vaccine that can be used prophylactically as well as therapeutically against two most important intracellular pathogens endemic in India, the tuberculosis and Leishmaniasis.

Another object is to use the motor domain region of the kinesin gene from Indian isolate of *Leishmania donovani* strain MHOM/IN/KE-16/1998 and esat-6 region of *Mycobacterium tuberculosis* Rv strain.

Yet another object is to generate chimeric molecule by ligating the genes identified as SEQ ID. No. 1 and SEQ ID. No. 2 on two sides of the gene coding for self cleaving peptide identified as SEQ ID No. 3.

Still another object is to clone the above chimeric molecule in DNA vaccine vector pVAX-1 (Invitrogen) amenable to translation by the eukaryotic cellular machinery (ribosomes, tRNAs, and other translation factors).

Yet another object is to study the in-vitro expression of the above construct.

Yet another object of this invention is to study the immunogenicity of the DNA chimeric vaccine construct consisting of SEQ ID NO: 1 and SEQ ID NO: 2 in BALB/c mouse model and higher animal and finally in humans.

Still another object of this invention is to provide a DNA vaccine candidate consisting of above mentioned construct operably linked to transcription regulatory elements wherein upon administration mammals and humans are protected from infections of *Mycobacterium spp* and *Leishmania spp*.

This invention relates to a novel recombinant chimera of DNA construct having esat-6 region of *Mycobacterium tuberculosis* and kinesin region of *Leishmania donovani* cloned together on two sides of self cleaving peptide in a DNA vaccine vector pVAX-1 wherein the Chimeric construct is operatively linked to a transcriptional promoter thus capable of self replication and expression within the mammalian cell and the process of preparation there of comprising. Analysis of the predicted protein sequence of kinesin motor domain and esat-6 domain using Promiscuous MHC Class-1 Binding Peptide Prediction Servers. Amplification of gene coding for kinesin motor domain and esat-6 domain. Cloning of kinesin esat-6 gene region in pGEM-T® vector for sequence analysis. Generation of Chimeric construct by directional cloning in pVAX-1 vector. In-vitro expression analysis of kinesin motor domain and esat-6 domain from the clones using cell free translation system and immunogenicity studies, Splenocyte proliferative and cytokines studies using the above mentioned constructs.

BRIEF DESCRIPTION OF ACCOMPANYING DRAWINGS

FIG. 1: Analysis of the predicted protein sequence of kinesin motor domain and ESAT-6 domain using Promiscuous MHC Class-I Binding Peptide Prediction Servers.

FIG. 2: (A) Amplification of kinesin motor domain, B) Amplification of esat-6 region.

FIG. 3: Restriction analysis of the clones having the motor domain region of kinesin gene of *Leishmania donovani* and esat-6 region of *Mycobacterium tuberculosis* cloned separately in pGEM-T® vector for sequencing and verification. Lane M: 100 bp Molecular Weight Marker (MBI Fermentas); Lane 1 & 4: Clones having kinesin motor domain as insert; Lane 5: Clone having esat-6 (Rv-3875) gene as insert; Lane 2, 3 & 6: Empty Plasmid.

FIG. 4: Generation of Chimera molecule Chimera construct and their specific restriction sites.

FIG. 5: pVAX-1-LDMT vector map with chimeric construct.

FIG. 6: Restriction analysis of the chimeric pVAX-1® clones having kinesin motor domain region and esat-6 region cloned together on two side of self cleaving FMDV-2A peptide. Lane 1, 2 & 5: Chimera with Kinesin (BstX1 & Apa 1); Lane 3: Chimera with Kinesin and FMDV (BamH1 & ApaI); Lane 4, 6 & 7: Chimera with esat-6 (Hind III & BamH1); Lane 8: 100 bp Marker (MBI®).

FIGS. 7A & 7B: Restriction analysis of the individual pVAX-1® clones having kinesin motor domain region and esat-6 region cloned. FIG. 7A, Lane 1: 100 bp Marker (MBI®); Lane 2 & 3: pVAX1 with Kinesin; Lane 4 & 5: Empty Plasmid; FIG. 7B, Lane 1: 100 bp Marker MBI®; Lane 2&3: Empty Plasmid; Lane 4& 5: pVAX1 with esat-6.

FIG. 8: In-vitro expression analysis of the clones using cell fee translation system.
(A) Western Blot analysis of In-vitro expression of Kinesin motor domain. Lane M: Prestained Molecular Weight Marker (MBI®; Lane 1 & 2: In-vitro expression of Kinesin from Chimeric construct; Lane 3: In-vitro expression of Kinesin from individual Kinesin-pVAX1 construct; Lane 4: Purified rLvacc probed with VL positive patient serum.
(B) Western Blot analysis In-vitro expression of ESAT-6 domain. Lane M: Prestained Molecular Weight Marker (NEB®); Lane 1 & 2: In-vitro expression of ESAT-6 from chimeric construct; Lane 3: In-vitro expression of ESAT-6 from individual ESAT-6-pVAX1 construct; Lane 4: Purified ESAT-6 probed with TB positive patient serum, FIG. 9: Splenocyte Proliferation Assay FIG. 10: IFN-γ, IL-2, IL-4 Response to vaccination.

FIG. 11: DTH response to kinesin motor domain and ESAT-6 in chimeric vaccine construct injected mice group.

BRIEF DESCRIPTION OF THE SEQUENCES IN THE SEQUENCE LISTING

SEQ ID NO: 1 is the nucleotide sequence of kinesin motor domain gene from Indian isolate of *L. donovani* strain MHOM/IN/KE-16/1998.

SEQ ID NO: 2 is the nucleotide sequence of esat-6 gene from *Mycobacterium tuberculosis* Rv strain.

SEQ ID NO: 3 is the nucleotide sequence of 2A peptide gene sequence from Foot and Mouth Disease Virus (FMDV).

SEQ ID NO: 4 is the nucleotide sequence of full length chimeric construct Kinesin motor domain gene, esat-6 gene and FMDV 2A peptide gene.

SEQ ID NO: 5 is the amino acid sequence of chimeric construct.

SEQ ID NO: 6 is the synthetic oligonucleotide, LF, SEQ ID NO: 7 is the synthetic oligonucleotide, LR, SEQ ID NO: 8 is the synthetic oligonucleotide, ESAT-F, SEQ ID NO: 9 is the synthetic oligonucleotide, ESAT-R.

DESCRIPTION OF THE INVENTION

The present invention provides a single vaccine candidate for control of leishmaniasis and tuberculosis. This invention also provides plasmid construct molecule which, when directly introduced into a vertebrate in vivo, including mammals such as humans induces the expression of two encoded proteins simultaneously within the animal. The embodiment comprises of construct of SEQ ID 1 and SEQ ID 2 joined on two side of SEQ ID 3 and cloned in mammalian expression vector pVAX-1. The idea is that the plasmid is taken up by cells and translocated to nucleus, where it is amenable to translation by the eukaryotic cellular machinery (ribosomes, tRNAs, and other translation factors). The efficiency of uptake and the expression of plasmid DNA may be low, but there is abundant evidence that it is sufficient to provoke immune response in both T and B cells.

There are several advantages of immunization with a gene rather than its gene product. The first is the relative simplicity with which native or nearly native antigen can be presented to the immune system. Mammalian proteins expressed recombinantly in bacteria, yeast, or even mammalian cells often require extensive treatment to insure appropriate antigenicity. A second advantage of DNA immunization is the potential for the immunogen to enter the MHC class I pathway and evoke a cytotoxic T cell response.

The first step toward development of any vaccine involves selection of specific candidate for vaccine development. On the basis of previous studies and in-silico analysis of the amino acid sequences mentioned in SEQ ID No. 5, using MHC-I-prediction software which predicts epitope for various HLA types we selected Kinesin Motor domain and ESAT-6 domain as candidate for chimeric DNA vaccine (FIG. 1).

Parasites were initially isolated as Promastigotes in NNN medium from clinical samples of Kala-azar patients and subsequently adapted to grow at 25° C. in Medium 199 containing 10% heat inactivated FCS. For routine maintenance, samples of the inoculum containing parasites were introduced aseptically into culture tubes with 4 ml of medium 199 supplemented with 10% FCS. The tubes were placed in BOD incubator at 25° C. and the growth was monitored at regular intervals by microscopy.

For mass cultivation of the parasite, samples of inoculum containing parasites were introduced aseptically into 200 ml of M199 containing 10% FCS in a 500 ml tissue culture flask and incubated in a cooled incubator at 25° C. until mid log phase (7-10 days). The parasites were then harvested and used for nuclear DNA isolation.

The parasites in their mid log phase was harvested by centrifuging at 5000 rpm in a refrigerated centrifuge. Parasite nuclear DNA was isolated following standard protocol with minor modifications. Approximately $1\text{-}5 \times 10^9$ promastigotes were lysed in 10 volumes of lysis buffer (NaCl, 100 mM, Tris-HC1, 10 mM (pH 8.0), EDTA 10 mM, Proteinase K/ml 100 pg, Sarcosyl 1.5%) at 60° C. for 3 hours. The kinetoplast DNA networks were sedimented by centrifugation at 27,000×g for 1 hour and resuspended in TE buffer (Tris-HC1 (pH 8.0) 10 mM, EDTA (pH 8.0) 1 mM). The nuclear DNAs were isolated from the supernatants left after sedimentation of the kDNAs. These supernatants were incubated overnight for further digestion of proteins at 65° C. The nuclear DNA was subjected to several cycles of phenol/chloroform extractions by adding equal volume of phenol/chloroform mixture, mixing thoroughly followed by sedimentation by centrifugation at 5000 rpm for 15 minutes. The nuclear DNA was precipitated by adding $\frac{1}{10}^{th}$ the volume of 3M-sodium acetate and 2 volumes of 100% ethanol mixed well and incubated at −20° C. for 1 hour. The mixture was sedimented by centrifugation at 5000 rpm for 30 minutes at 4° C. The pellet was washed with 70% ethanol, dried and resuspended in TE buffer. The concentration and purity of the DNA was measured by taking OD at 260/280 nm. The DNA was stored at −70° C. until use.

Similarly Rv strain of *Mycobacterium tuberculosis* was maintained on LJ culture medium. For DNA isolation few isolated colonies were selected from LJ slant and resuspended in TE buffer. DNA isolation was carried out according to the standard protocol 100 µl of pelleted culture was suspended in 400 µl of TE buffer and proceed for DNA isolation. The sample was then boiled at 100° C., followed by treatment with lysozyme, SDS and Proteinase K was given. The sample was then vortexed and incubated with CTAB. The nuclear DNA was subjected to several cycles of phenol/chloroform extractions by adding equal volume of phenol/chloroform mixture, mixing thoroughly followed by sedimentation at 10,000 rpm for 5 minutes. The nuclear DNA was precipitated with isopropanol. The mixture was sedimented by centrifugation at 10,000 rpm for 5 minutes at 4° C. The pellet was washed with 70% ethanol, dried and resuspended in TE buffer.

The PCR for the amplification of kinesin and esat-6 gene was performed as below using 50 ng of the isolated nuclear DNA. For kinesin gene the primes were designed based on the sequence data from the GenBank for the kinesin gene (Accession No. AY615866). The available kinesin gene sequence from *L. donovani* KE-16 strain is 2967 bp in length and has an ORF from position 361 with a putative ATG starting codon and extends until the last base at position 2967. The primers with SEQ ID No. 6 and SEQ ID No. 7 were designed to amplify the kinesin motor domain region. For amplification of esat-6 region patented primers as mentioned in SEQ ID No. 8 and 9 of the author himself with WIPO patent no. WO/2005/061730 was used with minor modifications.

By using aerosol free pipette tips and keeping the pre-and post-PCR products separately, amplicons carry over contamination was avoided. All PCR reactions were performed using standard protocols with a set of negative controls.

The cocktail for amplification of kinesin motor domain includes 10×Taq buffers 5.00 µl., 1.25 mM dNTPs 8.00 µl., Primer Forward (25 uM) 1.00 µl., Primer Reverse (25 µM) 1.00 µl, 0.5 µl Taq DNA polymerase (5 U/µl), Template DNA 3.00 µl., sterile water to make up the volume to 50.00 µl. The tubes were kept in thermal cycler (MJ Research, USA) followed by 30 cycles of amplification.

Similarly amplification of esat-6 region was carried out using 10×Taq buffer 2.5 µl, 1.25 mM dNTPs 4.00 µl, Primers forward (2 nM) 0.5 µl, Primer Reverse (2 nM) 0.5 µl, 0.5 µl. Taq DNA polymerase (5 U/µl), Template DNA 5.00 µl. sterile water to make up the volume to 25.00 µl. The tubes were kept in thermal cycler (MJ Research, USA) followed by 30 cycles of amplification.

The amplified PCR products were resolved on agarose gel electrophoresis. The gel was visualized under ultraviolet transilluminator (UVP) (FIGS. 2A & 2B).

The kinesin and esat-6 gene following amplification by PCR was cloned in a T A cloning vector. The PCR amplified DNA were resolved on agarose gel and the portion containing the band of interest was excised with a sterile scalpel. The DNA was eluted from the gel using gel elution kit (Qiagen, Germany) following the manufacturer's protocol. Concentration of eluted DNA was measured by absorbance at 260 nm in spectrophotometer.

The gel purified PCR product of interest was ligated directly in pGEMT-Easy vector. In a 0.5 ml micro centrifuge tube the following components were added. 2×rapid ligation buffer 5 µl, pGEM-T Easy vector (50 ng), 2.00 µl DNA (200 ng), 1.00 µl. T4 DNA Ligase (3 U/µl), water to make the volume up to 10.00 µl. After mixing gently, the tubes were incubated at 4° C. overnight and heated for 10 minutes at 70° C. The samples were stored at −20° C. until transformation.

The ligated mixture was than transformed by heat sock treatment. The competent cells JM-109 were prepared by using calcium chloride method. Approximately 5 µl of ligation mixture was gently mixed with competent cell 200 µl) and incubated in ice for 30 min. After incubation the cells were placed in water bath set at 42° C. for 90 seconds (heat shock) and immediately transferred to ice.

800 µl of LB medium was added to the cells and kept at 37° C. for 90 minutes with shaking (150 rpm). The cells were plated with 16 µl of X-gal and 10 µl of IM 1PTG on LB agar plates containing 100 µg/ml of ampicillin. The plates were incubated at 37° C. for 12-16 hours. The white colonies were selected and checked for the insert.

For screening plasmid was isolated by alkaline lysis method. For this the colonies were picked up with sterile toothpick and inoculated in 5 ml of fresh medium. The cultures grown overnight were pelleted and the cells were resuspended in 50 mM glucose, 25 mM tris-Cl, 10 mM EDTA (pH-8.0), after resuspending the pellets the cells are lysed by NAOH and 1% SDS, finally the solution is neutralized by adding Potassium acetate and glacial acetic acid. The cell lysates were pelleted down by centrifuging at 12000 RPM for 5 minutes. The supernatant was then subjected to several cycles of phenol/chloroform extractions by adding equal volume of phenol/chloroform mixture. Finally the plasmid DNA was precipitated with isopropanol. The mixture was sedimented by centrifugation at 10,000 rpm for 5 minutes at 4° C. The pellet was washed with 70% ethanol, dried and resuspended in TE buffer.

The restriction analysis of the recombinant Plasmid was done using appropriate restriction enzyme sites flanking the multiple cloning sites of the vectors. The reaction was set as follows: Plasmid DNA 16.00 μl (2 μg), 10×reaction buffer 4.00 μl, restriction enzyme 0.5 μl (2 units), Sterile water to make the volume up to 40.00 μl. The reaction was incubated at 37° C. for 6-8 hours and the products were analyzed on 1.5% agarose gel along with standard molecular weight markers (FIG. 3). The positive clones containing the insert as detected by the restriction digestion were used for sequencing and preserved as glycerol stock.

All the sequencing was done by chain termination method in an automated DNA sequencer, ABI Prism version 7.0. The Sequences were analyzed using various software like Clustal W (multile alignment of various sequence files), MHC prediction software. Along with this the sequence was searched for homology by using BLAST option from various websites.

Following sequence variation the next work that was carried out is the generation of chimeric molecule (FIGS. 4 & 5). For this the cloned fragment as referred as SEQ ID No. 1 and SEQ ID No. 2 were excised out by digestion with appropriate restriction enzyme. The FMDV 2A fragment designated as SEQ ID No. 3 was also digested out and ligated together with SEQ ID No. 1 & 2 (FIG. 4). The reaction was set as follows: 10×Buffer—2.5 μl, Kinesin motor domain-8 μl (1 μg), esat-6 gene—6 μl (1 μg), FMDV 2A region—3 μl (1 μg), T4 DNA ligase—1.5 μl (6 units), and sterile water to make up the volume to 25 μl. The ligation reaction was allowed to proceed to overnight at 4° C.

The chimeric molecule generated was purified and ligated together with pVAX1 vector (pVAX1-LDMT). The reaction was set as follows: 10×buffer—2.0 μl, Chimera molecule—15 μl (6 μg), pVAX-1 vector—2 μl (2 μg), T4 DNA ligase—1.0 μl (5 Units), and sterile water to make up the volume to 20 μl. (FIG. 5). After litigation recombination deficient and endonuclease deficient DH5 α-*E. coli* stain was transformed using pVAX1-LMDT with protocol as described above. The clones were selected on the kanamycin plates and plasmid DNA was isolated and digested with BstX1 and Apal (kinesin motor domain), BamH1 and Apal (Kinesin and FMDV regions), BamH1 and HindIII (esat-6 gene) to check for the insert (FIG. 6). Further confirmation was done using sequencing. The nucleotide sequence of the chimeric construct was mentioned in SEQ ID No. 4. The amino acid sequence deciphered from SEQ ID No. 4 is mentioned in SEQ ID No. 5.

Apart from chimeric construct individual constructs were generated by inserting SEQ ID No. 1 and SEQ ID No. 2 in pVAX-1 vector using protocol as described above. The individual constructs were generated to compare the efficacy of chimeric vaccine with individual vaccine candidates (FIGS. 7A & 7B).

For checking the proper litigation and expression of Sequences, in-vitro expression analysis was carried out using TNT coupled transcription/translation system (Promega). The reaction was set as follows: TNT quick master mix 40 μl, purified chimera-pYAX 1 construct (pVAX1-LDMT)—5 μl, nuclease free water to make up the volume to 50 μl.

In order to check the expression of kinesin motor domain and ESAT-6 domain, western blot analysis was carried out. The in-vitro reaction mixture of protein was resolved on 16% Tricine SDS-PAGE and transferred onto nitrocellulose membranes (Millipore) using a semi-dry blotting apparatus (Bio-Rad®, USA) following the instructions of the manufacturer. The membrane was blocked with 5% skimmed milk; washed thrice for 10 min each with PBS, pH 7.0, 0.1% Tween-20, then incubated for 1 h at room temperature with 1:50 dilution (in PBS, pH 7.0, 1% BSA) of patient sera and rabbit sera. The membrane was washed thrice with PBS, pH 7.0, 0.1% Tween-20, and then incubated for 1 h at room temperature with 1:1000 dilution of biotin-conjugated anti-human IgG (in PBS, pH 7.0, 1% BSA). Followed by incubation with secondary antibody the membrane was washed and then incubated with primary substrate avidine conjugated to horseradish peroxidase. After washing thrice for 10 min each with PBS, pH 7.0, 0.1% Tween-20, the blots were developed using a DAB (Amresco) and 0.1% $H_2O_2$ as substrate and bands were visualized directly on membrane (FIGS. 8A & 8B).

The immunogenicity study for the chimeric vaccine was carried out in inbred BALB/c mice model after having ethical approval from institute animal ethics committee. Six-to eight-week-old BALB/c mice were used in this study. Two days before DNA inoculation, the quadriceps muscles were injected with 100 μl. of a solution containing 0.25% bupivacaine hydrochloride to enhance subsequent DNA absorption. Four groups of 6 mice each were used for vaccination studies, cell proliferation, cytokine production and antibody response. The first group of mice was injected with chimeric construct. The second and third groups were injected with individual kinesin motor domain and esat-6 constructs, respectively. Mice injected with empty plasmid serve as control. For DNA inoculation, 100 μg of DNA construct in PBS was injected into the same region of the muscle as the bupivacaine injection. Two weeks after immunization, animals were given booster dose. Mice were sacrificed 2 weeks following the final injections and spleens from the mice in each group were dissected out, aseptically.

Spleens were removed from mice under aseptic conditions on a sterile dish containing RPMI 1640 media, Single cell suspensions were prepared by grinding the spleen with disk bottom of the plunger of 10 ml syringe. The 5-10 ml of RPMI-1640 medium was added to it and the contents were mixed to homogeneity. The dish was kept undisturbed for 2 min. and the clear supernatant was pipetted out slowly. Cells were pelleted by centrifugation at 4° C. at 250×g (Sigma Centrifuge) for 10 min. The pellet containing erythrocytes and splenocytes were collected. Washing the pellet once with 0.9% ammonium chloride lysed erythrocytes. The splenocytes left were than resuspended to a density of $2.5\times10^6$ cells/ml in RPMI 1640 containing 10% FCS and 0.05 μM 2-mercaptoethanol. From this $5\times10^5$ cells were added to 200 μl of RPMI-1640 media with 10% FCS in 96-well plates. The cells were stimulated with 1 μg/well of mitogen (Concavelin A), Kinesin and ESAT-6 antigen. The cells were than incubated for 48 hours at 37° C. in atmosphere containing 5% CO2 and 95% humidity. Proliferation was measured by MTT [3-(4,5-dimethylthiazol-2-yl)-2,5-diphenyltetrazolium bromide (Sigma Aldrich, St. Louis, Mo., USA)] assay as described elsewhere, with minor modifications [57]. In brief, MTT solution (10 μl, 5 mg/ml) was added to 200 μl of medium and incubated for 3 h at 37° C. After incubation the culture medium was removed and dark blue formazan crystals were dissolved in acidic isopropanol (100 μl. of 0.04 N HC1 in isopropanol). Color formation was measured at 570 nm, using ELISA plate reader (Biotek Instrument, USA). Wells with Concavalin A served as positive control while wells without any stimulant served as negative control (FIG. 9).

The level of 1FN-γ, IL-2 & IL-4 were also determined in culture supernatant using Endogen mouse 1FN-γ, IL-2 and IL-4 ELISA kit (Pierce Biotechnology, Inc. USA) according to manufacturer protocol (FIG. 10).

The above experiments revealed that Chimeric DNA vaccination generated cellular immune response against the expressed proteins resulting in the production of significant higher levels of 1FN-γ and IL-2 (TH-1), and lower levels of IL-4 (TH-2). Observations have also shown that vaccination with chimeric DNA resulted in generation of cellular immunity, which was superior to the individual vaccine molecules encoding ESAT-6 or Kinesin Motor protein (FIGS. 9 & 10).

The observations, reported here also suggest that the chimeric vaccine may represent an effective vaccine strategy against *L. donovani* and *M. tuberculosis* co-infection. Moreover co-expression of both the gene results in generation of strong cellular immunity, suggesting the adjuvant affect of both proteins over each other. Further protection studies are needed to consolidate the above observation.

The following examples are provided to illustrate the present invention without, however, limiting the same thereto.

EXAMPLE 1

Selection of Genes for Development of Chimeric Construct

In the process of development of a chimeric vaccine construct the first step involves the isolation of genes. Three gene regions were selected for preparation of this construct. This includes the esat-6 gene of *Mycobacterium tuberculosis*, Kinesin motor domain region of *Leishmania donovani*, and Foot and Mouth Disease Virus 2A peptide gene sequence.

The ESAT-6 antigen coded by esat-6 gene is one of the major secreted proteins found in *M. tuberculosis* culture filtrates and is a dominant target for cell-mediated immunity in the early phases of infection in TB patients and in various animal models. The esat-6 gene of *Mycobacterium tuberculosis* belongs to esat-6 multigene family and has five copies of a cluster of five copies of a cluster of esat-6 loci. These clusters contain members of the CFP-10 (1 hp) and ESAT-6 (esat-6) gene families (encoding secreted T-cell antigens) as well as genes encoding secreted, cell-wall-associated subtilisin-like serine proteases, putative ABC transporters, ATP-binding proteins and other membrane-associated proteins. This membrane associated and energy-providing proteins may function to secrete members of the ESAT-6 and CFP-10 protein families, and the proteases may be involved in processing the secreted peptide. This gene cluster was also conserved among other strains of *Mycobacterium*. Thus developing recombinant vaccine based on esat-6 gene loci may provide protective response against other pathogenic strains of *Mycobacterium* also.

Work has already been done to show the efficacy of ESAT-6 as suitable candidate for vaccine development. Among the various vaccines developed based on ESAT-6 till date includes recombinant BCG having esat-6 gene insert within, esat-6 subunit vaccine, and conjugate DNA vaccine having *Mycobacterium tuberculosis* genes MPT64, AG85B, and ESAT-6 as candidate antigen. All these vaccines developed have shown good efficacy and promised to be one of the future candidate for vaccination against *Mycobacterium tuberculosis*.

The candidate kinesin motor domain region of *L. donovani* selected is already known for inducing Th-1 specific response in mice model. Apart from that earlier in-silico analyses have revealed that it has cluster of MHC-I & II binding epitopes clusters in its peptide sequence [4]. The gene coding for kinesin motor domain of *Leishmania donovani* is a member of kinesin protein superfamily. In *Leishmania donovani* it has been found to play an important role in cell division and intracellular transports of various cargoes, including vesicles, organelles, large protein complexes, and cytoskeletal filaments and is highly conserved in nature both at nucleotide sequence and amino acid sequence level, demonstrating 80-90% identity with other *Leishmania* species and 35-45% identity in organisms such as trypanosomes, mouse and humans. In addition to its classical role, we have recently shown that immunodominant repeat region of the kinesin gene was highly sensitive and specific for diagnosis of leishmaniasis and was named as Ld-rkE16. Ld-rKE16 was found to be extremely (100%) specific with no false positive reaction in control sera. The analysis of Ld-rKE16 antigen in an ELISA format with sera from confirmed VL and PKDL patients from India, Pakistan and Turkey showed 100% sensitivity.

On the basis of the previous findings we carried out In-silica of the kinesin analysis using the two Promiscuous MHC Class-I Binding Peptide Prediction Servers. The servers predict the specific epitopes using neural network and on the basis of physiochemical properties of the epitope. The study revealed cluster of MHC-I binding epitopes that have high affinity for cytotoxic T-cells in kinesin motor domain region (FIG. 1). This let us to believe that kinesin may be a promising *Leishmania* vaccine candidate.

The 2A peptide of Foot and Mouth Disease Virus serves as linker molecule between kinesin and esat-6 gene. The reason for selection of this gene is that the peptide coded by this sequence serves as autoproteolytic element thus allowing individual expression of both esat-6 and Kinesin gene. It is its intrinsic property that makes it useful for chimeric expression of different genes.

EXAMPLE 2

Primer Designing for Isolating of Kinesin Motor Domain and esat-6 Gene

The primers capable of amplifying the coding regions of Kinesin motor domain and esat-6 genes have been developed. The primers are designed in such a way that they include restriction sites also for there efficient cloning in specific vector. The sequences of the primers for amplification of kinesin motor domain are mentioned in SEQ ID No. 6 and 7. Similarly the sequences of primers for amplification of esat-6 region are mentioned in SEQ ID No. 8 and 9.

Following there amplification using Pfu DNA polymerase they are cloned in pGEM-T vector, purified and analysed using automated sequencer (FIG. 3). Finally they are joined together on two sides of self cleaving peptide (2A peptide of FMDV) using specific adapter sequences with restriction sites, thus allowing individual expression of both genes from chimeric molecule. The details of synthesis of FMDV 2A peptide is mentioned below.

EXAMPLE 3

Synthesis of FMDV 2A Peptide

For above mentioned purpose, FMDV sequences having more than 90% percent cleavage activity were selected on the basis of database search. Finally on the basis of there length and restriction map for cloning in vector, 58 bp sequence with 97% cleavage activity was artificially synthesized from microsynth, Switzerland. The sequence of the gene was mentioned in SEC) ID No. 3.

EXAMPLE 4

Generation of Chimera Molecule

The cloned fragment as referred as SEQ ID No. 1 and SEQ ID No. 2 were excised out by digestion with restriction enzyme. The FMDV 2A fragment designated as SEQ ID No. 3 was also digested out and ligated together with SEQ ID No.

1 & 2 (FIG. 4). The ligation reaction was set as follows: 10×Buffer—2.5 µl, Kinesin motor domain—8 µl. (1 µg), esat-6 gene—6 µl (1 µg), FMDV 2A region—3µ. (1 µg), T4 DNA ligase—1.5 µl (6 units), and sterile water to make up the volume to 25 µl. The ligation reaction was allowed to proceed for overnight at 4° C.

EXAMPLE 5

Selection of Vector and Cloning of Chimera and Individual Genes in pVAX-1® Vector The DNA vaccine expressing protein of *Mycobacterium tuberculosis* and *Leishmania donovani* was prepared by introducing gene of *Mycobacterium tuberculosis* esat-6 region and *Leishmania donovani* kinesin motor domain region into mammalian expression vector under a strong promoter to drive the expression of the genes. The vector selected was pVAX-1® from invitrogen, a shuttle vector that can be screened easily using some bacterial strains (preferably *E. coli*). The other feature which makes the vector suitable for this application are that it have CMV promoter for high level expression in wide range of mammalian cell, BGH polyadenylation signal for efficient transcription termination and polyadenylation of mRNA, kanamycin resistant gene for selection thus minimizing allergic response and lastly the most important feature it has been cleared by FDA for its application as DNA vaccine for preventive infectious diseases.

The cloning of chimera molecule in pVAX-1 was carried out using basic cloning strategy. Both chimera molecule and pVAX1 vector was linearized by restriction digestion. Followed by the molecules was ligated using T4 DNA ligase. The reaction was set as follow: 10×buffer—2.0 µl, Chimera molecule—15 µl. (6 µg), pVAX-1 vector—2 µl. (2 µg), T4 DNA ligase—1.0 µl (5 Units), and sterile water to make up the volume to 20 µl (FIG. 5). After ligation recombination deficient and endonuclease deficient DH5 α-*E. coli* strain was transformed using pVAX1-LDMT with protocol as described above.

Apart from chimeric construct individual constructs were also generated by cloning esat-6 and kinesin motor domain gene in pVAX-1 using protocol as described above. All the recombinant molecules generated were screened using antibiotic pressure selection. Finally the plasmid DNA was purified from the recombinant colonies. The method includes alkaline lysis, RNase treatment, isopropanol precipitation and finally purification using suitable purification Kit.

Further analysis of the purified plasmid molecule was carried out using restriction digestion (FIGS. 6 & 7) and sequencing.

EXAMPLE 6

In-Vitro Expression Analysis of the Clones

The ability of the recombinant chimeric construct to express ESAT-6 and kinesin motor domain was studied in-vitro using TNT coupled transcription/translation system (Promega) according to the manufacturer's instruction. TNT uses a coupled transcription/translation reaction for in-vitro protein synthesis. Transcription and translation take place simultaneously in the reaction: while the RNA polymerase transcribes the template gene, the ribosomes provided by the TNT start to translate the 5'-end of nascent mRNA.

In order to check the expression of kinesin motor domain and ESAT-6 domain, western blot analysis was carried out. The in-vitro reaction mixture of protein was resolved on 16% Tricine SDS-PAGE and transferred onto nitrocellulose membranes (Millipore) using a semi-dry blotting apparatus (Bio-Rad®, USA) following the instructions of the manufacturer. The membrane was blocked with 5% skimmed milk; washed thrice for 10 min each with PBS, pH 7.0, 0.1% Tween-20, then incubated for 1 h at room temperature with 1:50 dilution (in PBS, pH 7.0, 1% BSA) of patient sera and rabbit sera. The membrane was washed thrice with PBS, pH 7.0, 0.1% Tween-20, and then incubated for 1 h at room temperature with 1:1000 dilution of biotin-conjugated anti-human IgG (in PBS, pH 7.0, 1% BSA). Followed by incubation with secondary antibody the membrane was washed and then incubated with primary substrate avidine conjugated o horseradish peroxidase. After washing thrice or 10 min each with PBS, pH 7.0, 0.1% Tween-20, the blots were developed using a DAB (Amresco) and 0.1% $H_2O_2$ as substrate, and hands were visualized directly on membrane (FIGS. 8A and 8B).

EXAMPLE 7

Immunogenicity of Chimeric and Individual Construct

Study on the immunogenicity of the chimeric construct using BALB/c mice model is in progress. The study includes vaccination of BALB/c mice followed by measurement of IFN-γ, IL-2 and IL-4 responses, Spleens were removed from vaccinated mice under aseptic conditions on a sterile dish containing RPM 1640 media. Single cell suspensions were prepared by grinding the spleen with disk bottom of the plunger of 10 ml syringe. The 5-10 ml of RPMI-1640 media was added to it and the contents were mixed to homogeneity. The dish was kept undisturbed for 2 min and the clear supernatant was pipetted out slowly. Cells were pelleted by centrifugation at 4° C. at 250×g (Sigma Centrifuge) for 10 min.

The pellet containing erythrocytes and splenocytes were collected. Washing the pellet once with 0.9% ammonium chloride lysed erythrocytes. The remaining cells were resuspended to a density of $2.5×10^6$ cells/ml in RPMI 1640 containing 10% FCS and 0.05 µM 2-mercaptoethanol, then divided into 200 µl aliquots ($5×10^5$ cells) in 96-well plates. After addition of mitogen (Concavelin A) and Kinesin, ESAT-6 antigen at 1, 5 & 10 µg/well concentration of Concavalin A and at 5 and 10 µg/well concentration of kinesin and ESAT-6 to each well, the cells were incubated for 3 days at 37° C. in atmosphere containing 5% $CO_2$ and 95% humidity. Proliferation was measured by Tetrazolium (MTT) assay (FIG. 9).

EXAMPLE 8

IFN-γ, IL-2 and IL-4 Detection in Splenocyte Culture of Mice in Response to Vaccination The splenocytes culture (isolated from mice) was set up in 96 well culture plates and $5×10^5$ cells/well were dispensed and antigens/mitogens were added to triplicate wells. At the end of 48 h, supernatant was harvested carefully from each well for cytokine determination. IL-2 and IL-4 in the supernatants was determined using an Endogen mouse IFN-γ, IL-2 and IL-4 enzyme-linked immunosorbent assay kit (Pierce Biotechnology, Inc. USA) as recommended by the manufacturer. The assays were calibrated to detect IFN-γ within the range of 20-3000 pg/ml (FIG. 10).

EXAMPLE 9

For DTH responses, footpad swelling was measured in naive BALB/c mice or mice injected with chimeric vaccine construct. Two months after boosting, each animal was injected in a hind footpad with 20 µg of total soluble protein of *Leishmania donovani* and *Mycobacterium tuberculosis* in 20 µl of PBS. Footpad swelling was measured with a dial caliper at various times, and the results were expressed as the difference between the thicknesses of the footpads inoculated with the antigen and the thickness of the footpads inoculated with 20 µl of PBS (FIG. 11).

SEQ ID NO. 1-
Kinesin Motor Domain Nucleotide Region-
5'ATGCACCCTTCCACTGTGCGGCGTGAGGCGGAGCGGGTGAAGGTGTCGGTG
CGCGTGCGCCCCCTAAACGAACGTGAAAACAATGCCCCGGAAGGGACGAAA
GTGACCGTTGCGGCGAAACAGGCGGCCGCCGTGGTGACGGTCAAGGTCCTGG
GAGGCAGCAACAACAGCGGCGCCGCCGAGTCGATGGGGACTGCAAGGCGGG
TAGCGCAGGACTTTCAGTTCGACCACGTGTTCTGGTCTGTGGAGACGCCGGA
CGCGTGCGGCGCGACCCCCGCGACGCAGGCAGACGTGTTCCGGACGATCGGG
TACCCGCTGGTGCAGCACGCGTTCGACGGGTTCAACTCGTGCTTGTTTGCGTA
CGGGCAGACAGGGAGCGGGAAGATGTACACGATGATGGGCGCGGACGTGAG
CGCGCTTAGTGGTGAGGGCAACGGCGTGACGCCGCGGATCTGCCTGGAGATC
TTTGCGCGGAAGGCGAGCGTGGAGGCGCAGGGGCACTCGCGGTGGATCGTG
GAGCTGGGGTACGTGGAGGTGTACAACGAGCGCGTGTCGGACCTGCTTGGGA
AGCGGAAGAAGGGTGTGAAGGGCGGCGGCGAGGAGGTGTACGTGGACGTGC
GCGAGCACCCGAGCCGCGGCGTGTTCCTGGAGGGGCAGCGGCTGGTGGAG
TTGGGAGCCTGGACGATGTTGTGCGGCTGATCGAGATCGGCAACGGCGTGCG
GCACACCGCTTCAACGAAGATGAACGACCGGAGCAGCCGGAGCCACGCGAT
CATCATGCTGCTGCGCGAGGAGCGGACGATGACGACGAAGAGCGGGGA
GACGATCCGTACTGCCGGCAAGAGCAGCCGCATGAACCTTGTGGACCTTGCG
GGGTCTAAGCGCGTGGCGCAGTCGCAGGTGGAGGGGCAGCAGTTCAAGGAG
GCGACGCACATCAACCTGTCGCTGACGACGCTCGGGCGCGTGATCGAC 3'

SEQ ID NO. 2-
esat-6 Nucleotide Region
5'ATGACAGAGCAGCAGTGGAATTTCGCGGGTATCGAGGCCGCGGCAAGCGC
AATCCAGGGAAATGTCACGTCCATATTCCCTCCTTGACGAGGGGAAGCAGTC
CCTGACCAAGCTCGCAGCGGCCTGGGGCGGTAGCGGTTCGGAGGCGTCCAGG
GTGTCCAGCAAAAATGGGACGCCACGGCTACCGAGCTGAACAACGCGCTGC
AGAACCTGGCGCGGACGATCAGCGAAGCCGGTCAGGCAATGGCTTCGACCG
AAGGCAACGTCACTGGGATGTTCGCA 3'

SEQ ID No. 3
FMDV 2 A Region-
5' GCG GAT CC AGA GCC GAG GGC AGG GGA AGT CTT CTA
    BamH1
ACA TGC GGG GAC GTG GAG GAA AAT CCC **CCA ATG CAT
TGGATG CAT**-3'
    BstX1

SEQ ID No. 4
Complete Nucleotide Sequence of Chimeric Construct

|     HindIII | |
|---|---|
| 5'CCCAAGCTTATGACAGAGCAGCAGTGGAATTTCGCGGGTATCGAGGCCGC<br>GGCAAGCGCAATCCAGGGAAATGTCACGTCCATATTCCCTCCTTGACGAGGG<br>GAAGCAGTCCCTGACCAAGCTCGCAGCGGCCTGGGGCGGTAGCGGTTCGGAG<br>GCGTCCAGGGTGTCCAGCAAAAATGGGACGCCACGGCTACCGAGCTGAACA<br>ACGCGCTGCAGAACCTGGCGCGGACGATCAGCGAAGCCGGTCAGGCAATGG<br>CTTCGACCGAAGGCAACGTCACTGGGATGTTCGCAGGATCCGC 3'<br>    BAMH1 | esat-6 |

| BAMH1 | |
|---|---|
| 5' *GCGGATCCAGAGCCGAGGGCAGGGGAAGTCTTCTAACATGCGGGGACGTG<br>GAGGAAAATCCCCCAATGCATTGGATGCAT 3'*<br>    BstX1 | FMDV |

| BstX1 | |
|---|---|
| 5'CCAATGCATTGGATGCACCCTTCCACTGTGCGGCGTGAGGCGGAGCGGGT<br>GAAGGTGTCGGTGCGCGTGCGCCCCCTAAACGAACGTGAAAACAATGCCCCG<br>GAAGGGACGAAAGTGACCGTTGCGGCGAAACAGGCGGCCGCCGTGGTGACG<br>GTCAAGGTCCTGGGAGGCAGCAACAACAGCGGCGCCGCCGAGTCGATGGGG<br>ACTGCAAGGCGGGTAGCGCAGGACTTTCAGTTCGACCACGTGTTCTGGTCTG<br>TGGAGACGCCGGACGCGTGCGGCGCGACCCCCGCGACGCAGGCAGACGTGTT | Kines |
| CCGGACGATCGGGTACCCGCTGGTGCAGCACGCGTTCGACGGGTTCAACTCG<br>TGCTTGTTTGCGTACGGGCAGACAGGGAGCGGGAAGATGTACACGATGATGG<br>GCGCGGACGTGAGCGCGCTTAGTGGTGAGGGCAACGGCGTGACGCCGCGGA<br>TCTGCCTGGAGATCTTTGCGCGGAAGGCGAGCGTGGAGGCGCAGGGGCACTC<br>GCGGTGGATCGTGGAGCTGGGGTACGTGGAGGTGTACAACGAGCGCGTGTCG<br>GACCTGCTTGGGAAGCGGAAGAAGGGTGTGAAGGGCGGCGGCGAGGAGGTG<br>TACGTGGACGTGCGCGAGCACCCGAGCCGCGGCGTGTTCCTGGAGGGGCAGC<br>GGCTGGTGGAGTTGGGAGCCTGGACGATGTTGTGCGGCTGATCGAGATCGG<br>CAACGGCGTGCGGCACACCGCTTCAACGAAGATGAACGACCGGAGCAGCCG<br>GAGCCACGCGATCATCATGCTGCTGCTGCGCGAGGAGCGGACGATGACGACG<br>AAGAGCGGGGAGACGATCCGTACTGCCGGCAAGAGCAGCCGCATGAACCTT<br>GTGGACCTTGCGGGGTCTAAGCGCGTGGCGCAGTCGCAGGTGGAGGGGCAGC | |

```
AGTTCAAGGAGGCGACGCACATCAACCTGTCGCTGACGACGCTCGGGCGCGT
GATCGACGGGCCC 3'
         Apa1
```

SEQ ID No. 5
Complete Amino Acid Sequence of Chimeric Construct
ESAT-6 Domain
MTEQQWNFAGIEAAASAIQGNVTSIHSLLDEGKQSLTKLAAAWGGSGSEAYQG
VQQKWDATATELNNALQNLARTISEAGQAMASTEGNVTGMFA
FMDV 2A Domain
RAEGRGSLLTCGDVEENPGP
Kinesin Motor Domain
MHPSTVRREAERVKVSVRVRPLNERENNAPEGTKVTVAAKQAAAVVTVKVLG
GSNNSGAAESMGTARRVAQDFQFDHVFWSVETPDACGATPATQADVFRTIGYP
LVQHHAFDGFNSCLFAYGQTGSGKMYTMMGADVSALSGEGNGVTPRICLEIFAR
KASVEAQGHSRWIVELGYVEVYNERVSDLLGKRKKGVKGGGEEVYVDVREHPS
RGVFLEGQRLVEVGSLDDVVRLIEIGNGVRHTASTKMNDRSSRSHAIIMLLLREE
RTMTTKSGETIRTAGKSSRMNLVDLAGSKRVAQSQVEGQQFKEATHINLSLTTL
GRVID SEQ ID No. 6 & 7
Synthetic Oligonucleotide LF and LR for amplification of Kinesin Motor Domain Region-
LF-Sense, 5'CCA ATG CAT TGG ATG CAC CCT TCC ACT GTG CGG 3'
BstX1
LR-Antisense, 5'GGG CCC GTC GAT CAC GCG CCC GAG CGT CGT 3'
Apa 1
(Primers selected from Kinesin gene sequence of *Leishmania donovani* KE-16 strain submitted in gene bank with accession number A Y615886, amplifying 361-1335 bp)

SEQ ID No. 8 and 9
Synthetic Oligonucleotide ESAT-F and ESAT-R for amplification of esat-6 gene-
Sense 5' CCC AAG CTT ATG ACA GAG CAG CAG TGG A 3'
HindIII
Antisense, 5' GCG GAT CCT GCG AAC ATC CCA GTG ACG 3'
Bam H1
(Primers selected from ESAT-6 gene sequence of *Mycobacterium tuberculosis* strain submitted in gene bank with accession number AF420491, amplifying 14-301 bp).

The invention claimed is:

1. A novel recombinant chimera of DNA construct comprising an esat-6 region of *Mycobacterium tuberculosis* and a kinesin region of *Leishmania donovani* cloned together on two sides of a self cleaving peptide in a DNA vaccine vector pVAX-1 wherein the chimeric construct is operatively linked to a transcriptional promoter and is capable of self replication and expression within a mammalian cell.

2. A pharmaceutically acceptable immune stimulatory preparation comprising a DNA sequence of a kinesin motor domain from *Leishmania donovani* and an esat-6 domain from *Mycobacterium tuberculosis*.

3. A method for stimulating an immune response in warm-blooded animals comprising administering the recombinant chimera of DNA construct of claim 1 via a percutaneous route and in an effective amount as pharmaceutical composition.

4. A method of stimulating a TH-1type immune response against both candidate genes comprising: providing the recombinant DNA construct of claim 1 to a subject.

5. A method of preparing a recombinant chimera of DNA construct comprising:
 a. analyzing the predicted protein sequence of kinesin motor domain and esat-6 domain using Promiscuous MHC Class-1 Binding Peptide Prediction Servers;
 b. amplifying gene coding for kinesin motor domain and esat-6 domain;
 c. cloning of kinesin esat-6 gene region in a vector for sequence analysis;
 d. generating chimeric construct by directional cloning in pVAX-1 vector; and
 e. performing in-vitro expression analysis of kinesin motor domain and esat-6domain from the clones using cell free translation system and immunogenicity studies, splenocyte proliferative and cytokines studies using the above mentioned constructs.

* * * * *